United States Patent [19]

Onoda et al.

[11] 3,959,354

[45] May 25, 1976

[54] PROCESS FOR PREPARING PHENYL ESTER

[75] Inventors: Takeru Onoda; Keisuke Wada, both of Yokohama, Japan

[73] Assignee: Mitsubishi Chemical Industries Ltd., Tokyo, Japan

[22] Filed: June 3, 1974

[21] Appl. No.: 475,894

[30] Foreign Application Priority Data

June 1, 1973 Japan................................ 48-61525

[52] U.S. Cl............................ 260/479 R; 252/430; 260/621 G
[51] Int. Cl.²......................................... C07C 67/00
[58] Field of Search .............................. 260/479 R

[56] References Cited
UNITED STATES PATENTS

| | | | |
|---|---|---|---|
| 3,644,486 | 2/1972 | Boldt et al. ..................... | 260/479 R |
| 3,646,111 | 2/1972 | Hornig et al. ................... | 260/479 R |
| 3,651,101 | 3/1972 | Boldt et al. ..................... | 260/479 R |
| 3,725,462 | 4/1973 | Boldt et al. ..................... | 260/479 R |

*Primary Examiner*—James A. Patten
*Attorney, Agent, or Firm*—Oblon, Fisher, Spivak, McClelland & Maier

[57] ABSTRACT

A phenyl ester and/or phenol is prepared by reacting benzene, a carboxylic acid and molecular oxygen in the presence of an improved catalyst comprising palladium metal, an antimony component and least one carboxylic acid salt of zinc, cadmium, lead or tin supported on a carrier.

9 Claims, No Drawings

PROCESS FOR PREPARING PHENYL ESTER

BACKGROUND OF THE INVENTION

1. Field of the Invention

This invention relates to a process for preparing a phenyl eser and/or phenol by reacting benzene, a carboxylic acid and molecular oxygen. This invention also relates to a new catalyst for the reaction.

2. Description of the Prior Art

The preparation of a phenyl ester and/or phenol from benzene, a carboxylic acid and molecular oxygen in the gas or liquid phase in the presence of a catalyst containing a noble metal of Group VIII of the periodic table, especially palladium, is known. It is also known that the catalytic activity can be improved by adding a weak acid salt of a strong base, such as an alkali metal salt of a carboxylic acid, as an auxiliary activator. It has been proposed to add a promotor such as gold, silver, copper, iron manganese or the like, which is not effective alone, to the palladium catalyst, in order to promote catalytic activity. The amount of the promotor is preferably a maximum of 50 atomic percent of palladium. (Japanese Patent Publication No. 33024/1971). It is also known that a carboxylic acid salt of a metal of Group IIb, III or IV of the periodic table is effective as an activator and a metal of Group Vb and VIb, especially tellurium or bismuth, is effective as a promotor. The amount of the promotor to precious metal is a maximum of 60 atomic percent, preferably 20–40 atomic percent. (British Patent No. 1,200,392 and British Patent No. 1,200,708). However, the known catalysts for preparing a phenyl ester from benzene, carboxylic acid and molecular oxygen, do not have enough catalytic activity for an industrial operation. Since an expensive noble metal, such as palladium, is used, there is a need for increasing catalytic activity per weight of palladium. The known catalysts have a further disadvantage of decreased catalytic activity in a short time in the gas phase reaction.

SUMMARY OF THE INVENTION

Accordingly, one object of the present invention is to provide a process for preparing a phenyl ester and/or phenol, avoiding the above-mentioned disadvantages, by using a catalyst having high catalytic activity and long catalytic life.

Another object of the invention is to provide a process for preparing a phenyl ester and/or phenol from benzene, a carboxylic acid and molecular oxygen in the gas phase by using a catalyst having high catalytic activity and long catalytic life.

These and other objects of the present invention as will hereinafter become more readily understood by the following description can be attained by using a catalyst composed of palladium metal, an antimony component and at least one of the carboxylic acid salts of zinc, cadmium, lead and tin.

DETAILED DESCRIPTION OF THE PREFERRED EMBODIMENTS

The catalyst used for the process of the invention contains three components: palladium metal, an antimony component and a metal carboxylate. As is clear from the following examples, the ratio of the antimony component to palladium metal highly affects the catalytic activity. The catalytic activity will decrease when the ratio of the antimony component to palladium metal is too high or too low. Accordingly, the antimony component is combined to the extent of 50–800 atomic percent, preferably 100–500 atomic percent as Sb, of palladium metal.

The third component of the catalyst is selected from carboxylic acid salts of zinc, cadmium, lead and tin, and preferably formates, acetates or propionates. The carboxylic acid salt of the same carboxylic acid used as the starting material is especially preferable. The amount of the carboxylic acid salt is usually 10–800 atomic percent, preferably 50–400 atomic percent as metal (Zn, Cd, Pb or Sn) of palladium metal. The three catalytic components are usually supported on a carrier. Various carriers can be used. Suitable carriers include silica gel, silica alumina, active carbon, alumina, clay, bauxite, magnesia, diatomaceous earth, pumice zeolite, or the like.

The content of palladium metal on the carrier can be selected from a broad range and is preferably 0.1 – 20% by weight. The reaction can be carried out even though the content of palladium is less than 0.1% by weight or more than 20% by weight. In the catalytic form, the palladium component is reduced to palladium metal. The antimony component is incompletely reduced to antimony oxide and antimony metal. At least part of the antimony metal forms an alloy with palladium metal. The zinc, cadmium, lead or tin component is the carboxylic acid thereof.

The preparation of the catalyst is not limited and can be carried out by conventional methods of preparing a metal catalyst supported on a carrier. The catalyst is preferably prepared by supporting a suitable palladium compound and a suitable antimony compound on a carrier and reducing the compounds by a suitable method, and then supporting the carboxylic acid salt of zinc, cadmium, lead or tin on the carrier. For example, the palladium compound and the antimony compound may be dissolved in a suitable solvent, the carrier is dipped into the solution, and the solvent is evaporated to affix the palladium compound and antimony compound to the carrier. The compounds on the carrier are then reduced in he gas phase with hydrogen gas, a reducing gaseous organic compound or by a conventional reducing agent such as hydrazine, formaldehyde, or the like. Alternatively, the carrier may be dipped into the solution of the palladium compound and the antimony compound, a precipitant, such as alkali, is added to the solution to precipitate the palladium component and the antimony component, and then the components on the carrier are reduced. The palladium component and the antimony component can be supported on the carrier simultaneously or separately. The carboxylic acid salt of zinc, cadmium, lead or tin is supported on the carrier already supporting the palladium metal and the antimony component, to give the final catalyst.

Suitable palladium compounds used for the preparation of the catalyst include halides, e.g. palladium chloride; organic acid salts, e.g. palladium acetate; palladium nitrate, palladium oxide and the like. Other palladium compounds, such as sodium palladium chloride, palladium acetylacetonate, or others may also be used.

Suitable antimony compounds used for the preparation of the catalyst include halides, e.g. antimony chloride; antimony oxide, antimony sulfite, or the like. Antimony metal, if desirable, may also be used.

Suitable carboxylic acid starting materials for preparing the phenyl ester and/or phenol from benzene, the carboxylic acid and molecular oxygen, include aliphatic, alicyclic and aromatic carboxylic acids. In the industrial process, a lower alkyl carboxylic acid, such as acetic acid, propionic acid, butyric acid, or the like is advantageous.

When acetic acid is used as the carboxylic acid, the reaction is conducted as follows:

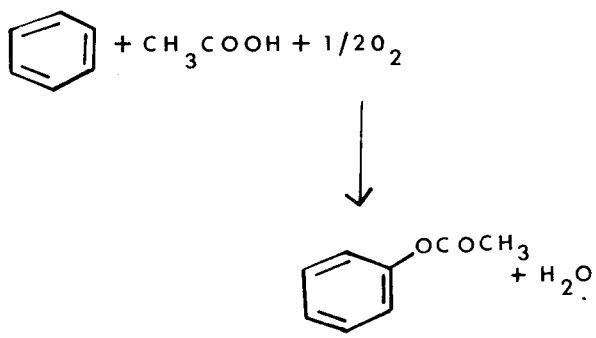

The reaction of benzene with the carboxylic acid and oxygen according to the invention is preferably performed in the gas phase. The reaction can be performed in a liquid phase, however, the zinc, cadmium, lead or tin carboxylic acid salt component of the catalyst will be eluted into the liquid phase since the carboxylic acid is present in the medium in the liquid phase. A part of the palladium may also be eluted from the catalyst. As a result, the carboxylic acid salt must be separated from the product and the eluted costly palladium metal must be recovered. Accordingly, liquid phase reactions are disadvantageous for an industrial process.

The reaction can be performed in any desirable system, such as a fixed bed system, a fluidized bed system, or the like. A fixed bed multipipe reactor is especially preferable to perform the highly exothermic reaction safely.

The molecular oxygen used for the reaction can be pure oxygen as well as oxygen diluted with an inert gas such as air. The amount of oxygen may vary, and is usually outside of the explosive range, and is preferably 1 – 50 mole percent of the total gaseous components. The reaction is performed under atmospheric pressure up to 20–30 atm, and may be performed under even higher pressure. The reaction temperature is dependent upon the boiling point of the carboxylic acid, the reaction pressure and the ratio of the starting materials, since the system is maintained in the gas phase, and is usually higher than 130°C. By giving consideration to the reaction velocity and side reactions, the preferable reaction temperature ranges from 140° – 250°C.

The ratio of benzene to the carboxylic acid can be selected from a broad range. An excess of the carboxylic acid is preferable for extending the catalytic life. Preferably molar ratios of benzene to the carboxylic acid are 1 : 1–10. As stated above, in accordance with the invention, the catalyst imparts significant catalytic activity, compared with conventional catalysts, and excellent selectivity for the object compound in the preparation of phenyl esters from benzene and a carboxylic acid. Only a small amount of phenol is formed by side reaction, and there is no by-product from coupling having a high boiling point, such as biphenyl, which may adversely affect the catalytic life. The advantages of the invention are thus clear.

A further understanding can be attained by reference to certain specific Examples which are provided herein for purposes of illustration only and are not intended to be limiting in any manner, unless otherwise specified.

EXAMPLE 1

A 50 cc amount of silica (16–30 mesh) was dipped into 50 ml of aqua regia (3 parts by volume of conc. HCl and 1 part by volume of conc. HNO$_3$) containing 4.58 mmole of palladium chloride and 16.0 mmole of antimony chloride, and the mixture was gradually concentrated and dried. The resulting solid produce was added to 50 ml of 15% aqueous hydrazine solution and was heated at 40°C for 8 hours to reduce the reduceable components. The supernatant solution was removed by decantation. The solid product was washed with enough distilled water to remove the hydrazine completely. A solution of 7.47 mmole of zinc acetate dissolved in 75 ml of hot water was added to the solid product and the mixture was gradually concentrated and dried with an evaporator. The resulting catalyst contained 2% by weight of palladium metal, 8% by weight of antimony metal and 2% by weight of zinc acetate. 10 cc of the catalyst was placed in a reaction tube made of glass having an inner diameter of 20 mm. A gaseous mixture of glacial acetic acid (20 ml/hr as liquid), benzene (20 ml/hr as liquid) and oxygen (840 ml/hr as gas) was passed through the reaction tube to effect continuous reaction at 200°C. The amounts of the products formed during each hour after 2 hours from initiation of the reaction are shown in terms of mole/mole Pd. hr. in Table 1.

REFERENCE EXAMPLE 1

The process of Example 1 was repeated except that the catalyst was prepared without adding antimony chloride. The results are shown in Table 1.

EXAMPLE 2

The process of Example 1 was repeated except that the catalyst was prepared by adding 4.11 mmole of stannous acetate instead of zinc acetate. The results are shown in Table 1.

EXAMPLE 3

The process of Example 1 was repeated except that the catalyst was prepared by adding 2.35 mmole of lead acetate instead of zinc acetate. The results are shown in Table 1.

EXAMPLE 4

The process of Example 1 was repeated except that the reaction temperature was 160°C. The results are shown in Table 1.

EXAMPLES 5 and 6

The process of Example 1 was repeated except that each catalyst was prepared by adding 3.74 mmole and 29.92 mmole of zinc acetate, respectively. The results are shown in Table 1.

EXAMPLE 7

A 10 cc quantity of the catalyst prepared by the process of Example 1 was placed in the reaction tube. A gaseous mixture of cyclohexane (8.0 ml/hr as liquid), acetic acid (25.6 ml/hr as liquid), benzene (6.4 ml/hr as liquid) and oxygen (890 ml/hr as gas) was passed through the reaction tube to effect continuous reaction at 220°C. The results are shown in Table 1.

EXAMPLE 8

A 10 cc quantity of the catalyst prepared by the process of Example 1 was placed in the reaction tube. A gaseous mixture of distilled water (2.0 ml/hr as liquid), cyclohexane (6.0 ml/hr as liquid), acetic acid (25.6 ml/hr as liquid), benzene (6.4 ml/hr as liquid) and oxygen (890 ml/hr as gas) was passed through the reaction tube to effect continuous reaction at 220°C. The results are shown in Table 1.

EXAMPLE 9

The process of Example 1 was repeated except that the catalyst was prepared by using 50 cc of diatomaceous earth (16 - 30 mesh) as carrier and 4.73 mmole of palladium chloride, 16.54 mmole of antimony chloride and 7.72 mmole of zinc acetate, and a gaseous mixture of acetic acid (32 ml/hr as liquid), benzene (8 ml/hr as liquid) and oxygen (890 ml/hr as gas) was passed through the reaction tube filled with 10 cc of the catalyst. The results are shown in Table 1.

EXAMPLES 10 – 14

The process of Example 1 was repeated with the catalyst prepared by adding 0.20, 0.50, 4.00, 8.00, or 32.00 mmole, respectively, of antimony chloride. The results are shown in Table 1.

EXAMPLE 15

A 50cc amount of silica (30–60 mesh) was dipped into 50 ml of aqua regia containing 5.67 mmole of palladium chloride and 17.48 mmole of antimony chloride, and the mixture was gradually concentrated and dried with an evaporator. The resulting solid product was dried by passage of nitrogen gas at 150°C for 2 hours, and then hydrogen gas at 400°C for 1 hour to reduce the reduceable components. A solution of 8.16 mmole zinc acetate dissolved in 80 ml of hot water was added to the solid product and the mixture was gradully concentrated and dried with an evaporator. 10 cc of the catalyst was placed in the reaction tube and the proces of Example 9 was repeated. The amounts of the products formed during each hour after a centain time from initiation of the reaction are shown in terms of mole/mole Pd. hr. in Table 2.

EXAMPLE 16

The process of Example 15 was repeated with a catalyst prepared by reducing the palladium component and antimony component with nitrogen gas saturated with methanol (at room temperature) at 200°C for 2 hours and then at 400°C for 1 hours, instead of hydrogen gas. The results are shown in Table 2.

REFERENCE EXAMPLE 2

The process of Example 16 was repeated except that the catalyst was prepared without adding zinc acetate. The results are shown in Table 2.

Table 1

| | Pd (wt. %) | Sb (wt. %) | Zn(OAc)$_2$ (wt. %) | Temp. (°C) | Phenyl acetate (mol/mol Pd.hr) | Phenol (mol/mol Pd.hr) |
|---|---|---|---|---|---|---|
| Exp. 1 *1) | 2.0 | 8.0 | 2.0 | 220 | 3.47 | 0.15 |
| Ref. 1 *1) | 2.0 | — | " | 220 | 0.25 | 0.01 |
| Exp. 2 *1) | 2.0 | 8.0 | Sn(OAc)$_2$ 2.0 | 220 | 1.28 | 0.13 |
| Exp. 3 *1) | 2.0 | 8.0 | Pb(OAc)$_2$ 2.0 | 220 | 0.97 | 0.30 |
| Exp. 4 *2) | 2.0 | 8.0 | 2.0 | 160 | 0.42 | 0.01 |
| Exp. 5 *1) | 2.0 | 8.0 | 1.0 | 220 | 3.03 | 0.69 |
| Exp. 6 *1) | 2.0 | 8.0 | 8.0 | 220 | 3.42 | 0.08 |
| Exp. 7 *3) | 2.0 | 8.0 | 2.0 | 220 | 2.23 | 0.01 |
| Exp. 8 *4) | 2.0 | 8.0 | 2.0 | 220 | 1.94 | 0.01 |
| Exp. 9 *2) | 2.0 | 8.0 | 2.0 | 220 | 2.19 | 0.01 |
| Exp.10 *1) | 2.0 | 0.1 | 2.0 | 220 | 0.96 | 0.07 |
| Exp.11 *1) | 2.0 | 0.25 | 2.0 | 220 | 1.62 | 0.16 |
| Exp.12 *1) | 2.0 | 2.0 | 2.0 | 220 | 2.37 | 0.22 |
| Exp.13 *1) | 2.0 | 4.0 | 2.0 | 220 | 2.86 | 0.28 |
| Exp.14 *1) | 2.0 | 16.0 | 2.0 | 220 | 1.92 | 0.10 |

| Note | *1 | *2 | *3 | *4 |
|---|---|---|---|---|
| acetic acid (ml/hr. as liquid) | 20 | 32 | 25.6 | 25.6 |
| benzene (ml/hr. as liquid) | 20 | 8 | 6.4 | 6.4 |
| oxygen (ml/hr. as gas) | 840 | 890 | 890 | 890 |
| cyclohexane | | | 8.0 | 6.0 |
| water | | | | 2.0 |

Table 2

| | | Production of phenyl acetate (mole/mole Pd.hr) *1) | | |
|---|---|---|---|---|
| | | Exp. 15 | Exp. 16 | Ref. 2 |
| Reduction | | hydrogen | methanol | methanol |
| Pd | (wt.%) | 2.0 | 2.0 | 2.0 |
| Sb | (wt.%) | 8.0 | 8.0 | 8.0 |
| Zn(OAc)$_2$ | (wt.%) | 2.0 | 2.0 | — |
| Amounts of phenyl acetate during each 1 hour after | | | | |
| 17 hours | | — | 3.5 | 3.9 |
| 20 " | | 3.3 | 3.9 | 3.0 |
| 24 " | | — | 4.0 | 2.1 |
| 31 " | | — | 4.3 | — |
| 38 " | | — | 4.4 | — |
| 50 " | | 3.2 | 4.6 | — |
| 100 " | | 3.2 | — | — |

| Note | *1) |
|---|---|
| acetic acid (ml/hr as liquid) | 32 |
| benzene (ml/hr as liquid) | 8 |
| oxygen (ml/hr as gas) | 890 |
| reaction temperature | 220°C |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for preparing a phenyl ester and/or phenol by reacting benzene, a carboxylic acid and molecular oxygen in the presence of a catalyst, the improvement which comprises:

conducting said reaction in the presence of a catalyst consisting essentially of 0.1–20 wt.% of palladium metal, an antimony component formed by incomplete reduction of antimony oxide to antimony oxide and antimony metal and present in amounts of 100–500 atomic percent as Sb based on palladium and at least one carboxylic acid salt of zinc, cadmium, lead or tin in an amount ranging from 10 to 800 atomic percent as the metal based on palladium supported on a carrier.

2. The process of claim 1, wherein the carboxylic acid salt of zinc, cadmium, lead or tin is a lower carboxylic acid salt selected from the group consisting of formate, acetate and propionate.

3. The process of claim 1, wherein the carboxylic acid salt of zinc, cadmium, lead or tin has a carboxylic acid component the same as the carboxylic acid used as the starting material.

4. The process of claim 1, wherein the content of zinc, cadmium, lead or tin is 50–400 atomic percent of the palladium metal in the catalyst.

5. The process of claim 1, wherein the carboxylic acid starting material is a saturated $C_{2-4}$ lower aliphatic carboxylic acid.

6. The process of claim 1, wherein the carboxylic acid is acetic acid.

7. The process of claim 1, wherein the molar ratio of benzene to carboxylic acid in the reaction is 1 - 10.

8. The process of claim 1, wherein the reaction is conducted at 140° – 250°C.

9. The process of claim 1, wherein the reaction is conducted in the gas phase.

* * * * *